United States Patent [19]

Nobbio

[11] Patent Number: Plant 6,089

[45] Date of Patent: Jan. 26, 1988

[54] CARNATION NAMED MEI SOL

[75] Inventor: Giacomo Nobbio, San Remo, Italy

[73] Assignee: Klemm & Sohn, Stuttgart-Muhlhausen, Fed. Rep. of Germany

[21] Appl. No.: 798,302

[22] Filed: Nov. 15, 1985

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of carnation, characterized by its profuse and continuous year-round production of Dianthus purple flowers of medium size, each petal of which is bordered with a smooth margin, of a magenta color. This plant has a vigorous and upright growth habit with peduncles shorter than those found in other carnations, having a length from 35–45 cm.

1 Drawing Figure

BACKGROUND OF THE NEW PLANT

This new carnation originated at San Remo, Italy as a seedling derived by my crossing plants selected from breeding stock maintained in my greenhouse at San Remo, Italy, the object of this crossing being the production of an improved carnation suitable for cut-flowers. In 1981, it was discovered that the plant possessed the precocity and color contrast that I was seeking. Asexual propagation of this new plant, by means of cuttings, has been carried out at Stuttgart, West Germany, and San Remo, by me and under my direction through successive generations and the distinctive characteristics of this plant has been found to hold true from generation to generation and appear to be firmly fixed.

DESCRIPTION OF THE DRAWING

My new variety of carnation plant is illustrated by the accompanying full color photographic drawing, which shows a group of flowering stems having buds in various stages of opening, newly opened flowers and blooms in further stages of maturity, the flower coloration being shown as nearly true as it is reasonably possible to obtain by means of conventional photographic procedures.

DESCRIPTION OF THE NEW PLANT

The following is a detailed description of my new carnation variety, based upon observation of the plants grown under conventional greenhouse practices, with color designations being according to The Horticultural Colour Chart published by the Royal Horticultural Society of London, England.

THE PLANT

Origin: Seedling.
Parentage:
- *Seed parent.*—Breeding Stock No. 824.
- *Pollen parents.*—Breeding Stock No. 712.

Classification:
- *Botanic.*—*Dyanthus caryophyllus.*
- *Commercial.*—Greenhouse carnation.

Form: Bush.
Height: About 70 to 90 cm.
Growth: Upright.
Strength: Moderate.
Branching: Normal.

Foliage:
- *Quantity.*—Moderate.
- *Leaf size.*—Small.
- *Leaf shape.*—Oblong.
- *Margin type.*—Entire.
- *Texture.*—Smooth.
- *Color.*—Upper side — blue green. Under side — blue green

THE BUD

Size: Small, about 12 to 15 mm. in diameter and about 20 mm. long.
Form: Cylindrical.
Shape: Ovoid.
Opening rate: Medium.
Color: When sepals first divide: white.
Calyx:
- *Size.*—Small.
- *Shape.*—Cylindrical.
- *Splitting.*—The calyx does not split.
- *Aspect.*—Smooth.

Sepals:
- *Number.*—Five to six.
- *Condition.*—Upstanding.
- *Color.*—Inside — light green; outside — gray green.

THE FLOWER

Blooming habit: Continuous and profuse.
Size of the bloom: Small.
- *Diameter.*—About 40–50 mm.
- *Depth.*—About 30–35 mm.

Borne: Singly.
Shape: High center at first opening and the form is not changed as the flower matures.
Petalage:
- *Number of petals.*—About 40–45.
- *Arrangement.*—Generally imbricated.
- *Form.*—Smooth margin.
- *Texture.*—Soft.
- *Appearance.*—Velvety.
- *Color.*—Outer petals Dianthus purple: H.C.C. 730/1 in the main body with lighter magenta colored margins.

Peduncle: Sturdy and upright.
- *Length.*—About 35–45 cm.
- *Color.*—Blue green.

*Persistence.*—The flowers hang on and dry; the bloom stays upright.

*Fragrance.*—None.

Lasting quality: On the plant, about 12 days; as a cut flower, about 8 to 10 days.

REPRODUCTIVE ORGANS

Stamens:

*Number.*—About 8 to 12.

Anthers:

*Color.*—Gray.

Filaments:

*Length.*—6 to 8 mm.

*Color.*—White.

Pollen:

*Color.*—Gray.

Pistils:

*Number.*—Two.

Styles:

*Length.*—6 to 8 mm.

*Color.*—White.

Stigmas:

*Color.*—White.

Fruit: Fertile.

*Shape.*—Ovoid.

*Color.*—Green/brown at maturity.

This new variety of carnation plant is particularly distinguished by the Dianthus purple coloring of its flowers which have petals with a smooth margin, the margin being lighter in color, approximating magenta. The flower has a closed calyx which is not split and the plant has an excellent capacity for continuous and profuse production of blooms, although the peduncle is shorter than those found in other carnations. The flower has good lasting quality after being cut.

I claim:

1. A new and distinct variety of carnation plant, substantially as herein shown and described, characterized by its high productivity of Dianthus purple flowers supported singly on a upright peduncle, the flowers being further characterized by having petals which have smooth margins of a light color, approximating magenta.

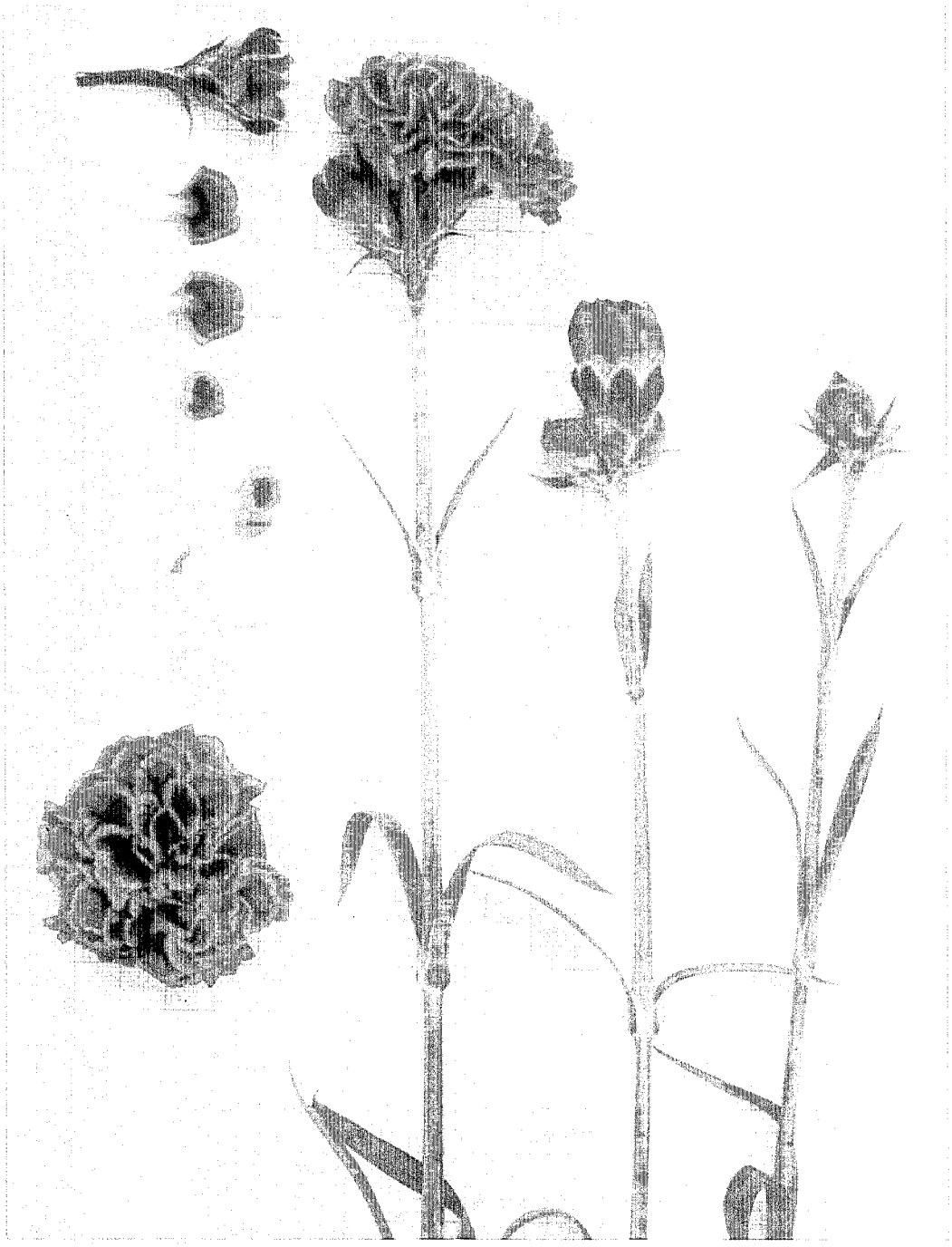

* * * * *